United States Patent
Palamidessi et al.

[11] 4,148,996
[45] Apr. 10, 1979

[54] 3,7-DISUBSTITUTED CEPHALOSPORINS

[75] Inventors: Giorgio Palamidessi; Franco Zarini; Giovanni Franceschi, all of Milan; Giovanna Schioppacassi; Federico Arcamone, both of Nerviano, all of Italy

[73] Assignee: Societa Farmaceutici Italia S.p.A., Milan, Italy

[21] Appl. No.: 797,606

[22] Filed: May 16, 1977

[30] Foreign Application Priority Data

May 21, 1976 [GB] United Kingdom ............... 21032/76

[51] Int. Cl.² .......................................... C07D 501/36
[52] U.S. Cl. .................................... 544/26; 544/27; 424/246
[58] Field of Search ..................... 544/26, 27; 424/246

[56] References Cited

U.S. PATENT DOCUMENTS

| 3,960,849 | 6/1976 | Breuer | 544/26 |
| 4,007,173 | 2/1977 | Hoover et al. | 544/26 |
| 4,016,159 | 4/1977 | Bormann et al. | 544/27 |
| 4,039,536 | 8/1977 | Takano et al. | 544/26 |

Primary Examiner—Nicholas S. Rizzo
Attorney, Agent, or Firm—Stevens, Davis, Miller & Mosher

[57] ABSTRACT

7-Acylamino-3-pyrazinylthiomethyl-3-cephem-4-carboxylic acids are disclosed having the general formula:

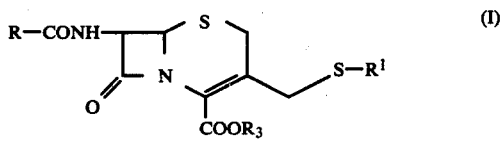

wherein R is an alkyl having from 1 to 5 carbon atoms or

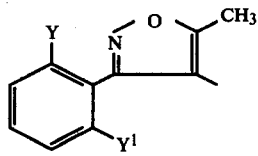

-continued

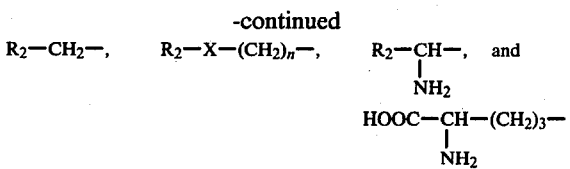

wherein
$Y = Y^1 = H$
$Y = Y^1 = Cl$
$Y = Cl, Y^1 = F$
$Y = H, Y^1 = Cl$ and in which n is an integer from 1 to 4, X is O or S, and $R_2$ is thienyl, phenyl, 1,4-cyclohexadienyl, phenoxy, pyrazinyl and substituted phenyl, thienyl, pyrazinyl and phenoxy, the substituent being selected from the group consisting of hydroxy, chlorine, bromine, and alkyl and alkoxy having from 1 to 4 carbon atoms;

$R_3$ is alkali metal such as sodium or potassium, hydrogen, alkyl having from 1 to 4 carbon atoms, benzyl, trichloroethyl, methoxybenzyl, benzhydryl, pivaloyloxymethyl, and an alkaline earth metal; $R^1$ may be a pyrazinyl of the general formulae:

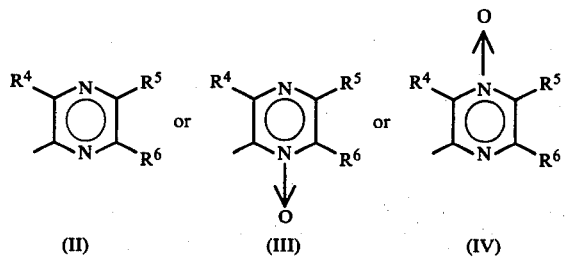

(II)    (III)    (IV)

in which $R^4$, $R^5$, $R^6$ are equal or different and are selected from the group consisting of F, Cl, Br, hydrogen, alkyl, phenyl, cyano, thiocyano, carboxyl, carboxyalkyl, carboxamido, thiocarboxamido, hydroxy, alkoxy, thiol, alkylthio, amino, alkylamino, phenylamino. By the terms alkyl, an alkyl having from 1 to 4 carbon atoms is intended. Processes for making them are also disclosed.

The new cephalosporin derivatives of formula (I) exhibit a broad spectrum antibacterial activity and are useful as therapeutic agents in the treatment of infectious diseases caused by gram-negative and gram-positive bacteria.

14 Claims, No Drawings

3,7-DISUBSTITUTED CEPHALOSPORINS

The present invention relates to new 3,7-disubstituted cephalosporins and to a process for the preparation thereof.

More particularly, it relates to 7-acylamino-3-pyrazinylthiomethyl-3-cephem-4-carboxylic acids having the general formula:

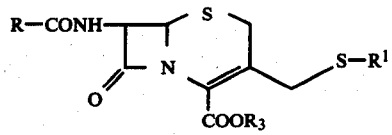

wherein R is an alkyl having from 1 to 5 carbon atoms

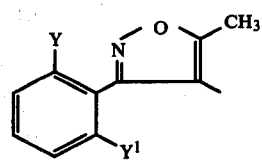

$R_2-CH_2-$, $R_2-X-(CH_2)_n$, $R_2-CH-$, and
$\qquad\qquad\qquad\qquad\qquad\qquad\quad\; NH_2$

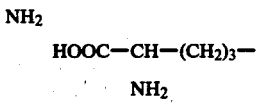

wherein
 Y=Y$^1$=H
 Y=Y$^1$=Cl
 Y=Cl, Y$^1$=F
 Y=H, Y$^1$=Cl and
in which n is an integer from 1 to 4, X is O or S, and $R_2$ is thienyl, phenyl, 1,4-cyclohexadienyl, phenoxy, pyrazinyl and substituted phenyl, thienyl, pyrazinyl and phenoxy, the substituent being selected from the group consisting of hydroxy, chlorine, bromine, and alkyl and alkoxy having from 1 to 4 carbon atoms;

$R_3$ is alkali metal such as sodium or potassium, hydrogen, alkyl having from 1 to 4 carbon atoms, benzyl, trichloroethyl, methoxybenzyl, benzhydryl, pivaloyloxymethyl and an alkaline earth metal; $R^1$ may be a pyrazinyl of the general formulae:

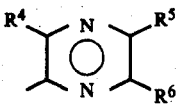

(II)

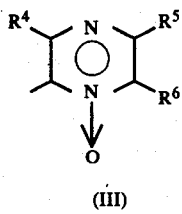

(III)

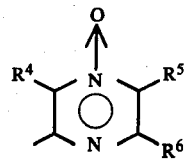

(IV)

in which $R^4$, $R^5$, $R^6$ are equal or different and are selected from the group consisting of F, Cl, Br, hydrogen, alkyl, phenyl, cyano, thiocyano, carboxyl, carboxyalkyl, carboxamido, thiocarboxamido, hydroxy, alkoxy, thiol, alkylthio, amino, alkylamino, phenylamino. By the term alkyl, an alkyl having from 1 to 4 carbon atoms is intended.

The new cephalosporin derivatives of formula (I) exhibit a broad spectrum antibacterial activity and are useful as therapeutic agents in the treatment of infectious diseases caused by gram-negative and gram-positive bacteria. For such purpose, they may be administered either parenterally or orally, both as acids and salts of pharmaceutically acceptable cations (e.g. sodium, potassium, calcium, magnesium).

Compounds of formula (I) are prepared by reacting various cephalosporins (V), including cephalosporin C, with appropriate mercaptopyrazines.

Alternatively, 3-thiomethyl compounds of formula (I) can be prepared by treating a 3-thiolated 7-ACA of formula (VI) with a suitable acylating agent (e.g., acid chloride, acid anhydride, acid azide, activated ester). The replacement of the acetoxy group of the cephalosporin derivative is carried out in the presence of an inert solvent (e.g. acetone, dioxane, methanol, ethanol, tetrahydrofuran) or in a mixture of these solvents in an aqueous solution thereof, in water or a buffer (e.g. borate, phosphate buffers) by following the widely known general procedure (see MURPHY C. F. and J. A. WEBBER: CEPHALOSPORINS AND PENICILLINS, Chemistry and Biology—E. H. FLYNN, Academic Press, New York, 1972, Chapter 4) which will be outlined in the examples below. The thiols can be used either in the free form or as metal salts. The compounds of formula (VI) (e.g. 3-thiolated-7-ACA) are prepared from both 7-aminocephalosporanic acid and cephalosporin C by reacting with a suitable mercaptopyrazine. When cephalosporin C is used as starting material, the resulting 3-thiolated cephalosporin C is hydrolysed according to well-known procedures (see F. M. HUBER, R. R. CHAUVETTE and B. G. JACKSON, reference cited above, Chapter 2) to give the desired 3-thiolated 7-ACA.

More particularly, the amide cleavage involves the use of phosphorous pentachloride on a protected system, such as the silylated 3-thiolated-cephalosporin C ester, and the initial imino chloride is transformed into the corresponding imino ether by reaction with an alcohol, to give after hydrolysis the desired 3-thiolated 7-ACA. On the silylated-protected compounds, see the book "Cephalosporins and Penicillins", edited by Edwin H. Flynn, Academic Press, New York, 1972, chapter 2, particularly pages 53 and 65, or British Pat. No. 1,244,191.

SYNTHESIS DIAGRAM

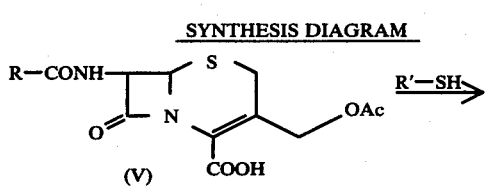

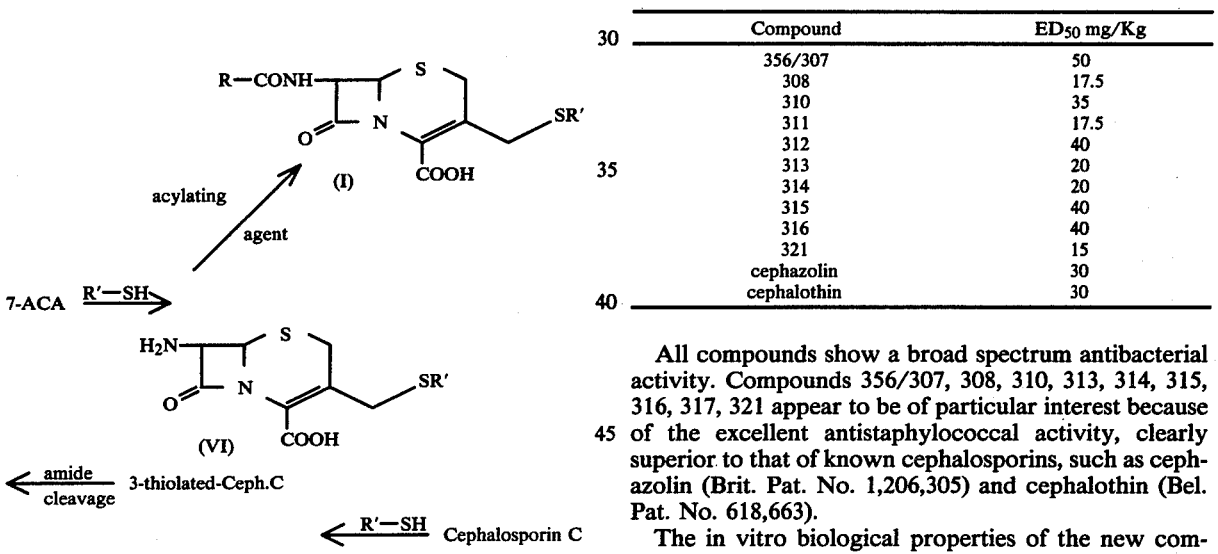

The intermediates of formula (VI) are new compounds.

Further objectives of the present invention are the corresponding acylamidomethyl-esters, acyloxymethyl-esters, 5-oxotetrahydro-2-furyl-esters, and phthalidyl esters of the acids of formula (I).

The new 3,7-disubstituted cephalosporin derivatives of formula (I) show a strong antibacterial activity against gram-positive and gram-negative bacteria.

A series of comparative tests was carried out in vitro with the method of serial dilutions in Penassay Seed Broth Difco inoculated with $10^4$ bacteria/ml (overnight cultures).

Table 1 below reports the results of the above assays as MIC (minimal inhibitory concentration, mcg/ml).

In vivo tests for therapeutic activity were carried out on mice experimentally infected with *Staphylococcus aureus* and *Salmonella abortivoequina* (Infective dose: 2 $LD_{50}$/mouse i.p.); groups of 6 male Swiss Cobs albino mice were used. The infected animals were treated by the subcutaneous route 4 h after infection. The mortality rate was recorded every day for 7 days. The activity was assessed as $ED_{50}$ (Dose effective in curing 50% of the infected mice as mg/Kg—see Reed and Muench, Am. J. Hyg. 27, 493, 1938.)

The results are reported in Table 2 below.

Table 1

| Compound | MIC/μg/ml | | | | | | | |
|---|---|---|---|---|---|---|---|---|
| | S.aureus | S.pyogenes | E.coli B | K.pneumoniae | S.flexneri | P.mirabilis | S.abortivoe-quina | S.typhimurium |
| 356/307 | 0.012 | 1.5 | 6 | 1.5 | 12.5 | | 25 | |
| 308 | 0.012 | 1.5 | 1-2 | 0.75 | 50 | 50 | 100 | |
| 310 | 0.06 | 6.2 | 0.6 | 0.1 | >50 | | 50 | |
| 311 | 0.06 | 1.5 | 5 | 1.5-2.5 | 12.5 | >50 | >50 | |
| 312 | 0.12 | 3.1 | 5 | 1.5 | 12.5 | | 25 | |
| 313 | 0.012 | 1.25 | 2.5 | 1.25 | 6.25 | 50 | 6.25 | 12.5 |
| 314 | 0.003 | 1.25 | 0.6 | 0.6 | 6.25 | 25 | 6.25 | 6.25 |
| 315 | 0.006 | 1.25 | 2.5 | 1.25 | 50 | >50 | >50 | >50 |
| 316 | 0.025 | 2.5 | 5 | 2.5 | 12.5 | >50 | 12.5 | 50 |
| 317 | 0.005 | | 1.5 | 1.5 | 50 | 50 | >50 | >50 |
| 318 | 0.097 | | 6.25 | 3.1 | 3.1 | 12.5 | 3.1 | 12.5 |
| 321 | 0.037 | 0.12 | 1.25 | 0.25 | 10 | 10 | 20 | 20 |
| cephalothin | 0.1 | 1.25 | 1.25 | 0.3 | 1.5 | 6.2 | 1.5 | 3 |
| cephazolin | 0.1 | 1.25 | 1.25 | 0.6 | 1.5 | 3.1 | 1.25 | 1.5 |

| Compound | $ED_{50}$ mg/Kg |
|---|---|
| 356/307 | 50 |
| 308 | 17.5 |
| 310 | 35 |
| 311 | 17.5 |
| 312 | 40 |
| 313 | 20 |
| 314 | 20 |
| 315 | 40 |
| 316 | 40 |
| 321 | 15 |
| cephazolin | 30 |
| cephalothin | 30 |

All compounds show a broad spectrum antibacterial activity. Compounds 356/307, 308, 310, 313, 314, 315, 316, 317, 321 appear to be of particular interest because of the excellent antistaphylococcal activity, clearly superior to that of known cephalosporins, such as cephazolin (Brit. Pat. No. 1,206,305) and cephalothin (Bel. Pat. No. 618,663).

The in vitro biological properties of the new compounds were verified by successful therapy of experimental mouse infections. In fact, compounds 356/308, 311, 313, 314, 321 proved to be more effective than cephazolin and cephalothin on the experimental staphylococcal infections.

The new compounds are generally less active on gram-negative bacteria. However compounds 314, 317, 321 demonstrated a therapeutic activity similar to that of cephalothin on *Salmonella abortivo equina* experimental infections of mice. In particular, the therapeutic activity of compound 321 on mice experimentally infected with *Salmonella abortivo equina* ($ED_{50}$ mg/Kg) proved to be equal to or slightly lower than that of cephalothin and cephazolin respectively (321=50; cephalothin=50; cephazolin=25); this behaviour suggesting different pharmacokinetics or a greater bioavailability of the new compound.

The following examples are illustrative but not limitative of the invention;

EXAMPLE 1

7-phenylacetamido-3-(6-carboxamidopyrazin-2-ylthiomethyl)-3-cephem-4-carboxylic acid (356/311)

A solution of 3 g of 7-phenylacetamidocephalosporanic acid, 1.3 g of 2-mercaptopyrazine, and 1.36 g of sodium bicarbonate in a mixture of 45 ml of water-acetone (2:1) was stirred for 3 hours at 65°–70° C.

The acetone was removed under reduced pressure and the aqueous solution was adjusted to pH 2.0 with 2 N HCl under cooling at 0°–5° C. The resulting crude precipitate was collected by filtration, washed with water, and crystallized from aqueous acetone to give yellowish crystals (2.6 g 70% yield), m.p. 142° C.

IR (KBr) 1775, 1705, 1690, 1655 cm$^{-1}$. (*) NMR methylester (CDCl$_3$/DMSO-d$_6$ 5/2): 3.80δ (s, COOCH$_3$), 3.33δ. (s, C(2)H$_2$), 3.61δ (s, C$_6$H$_5$—CH$_2$—CO), 4.41δ (dd, CH$_2$—S), 4.93δ. (d, C(6)H), 5.66δ (d, C(7)H), 7.0δ (s, C$_6$H$_5$), 8.56 and 8.88δ (two s, pyrazine protons).

(*)Owing to the insolubility of the free acids, in some of the examples the NMR spectra were run on their corresponding methylesters.

EXAMPLE 2

In the same manner as shown in Example 1, by using 7-phenylacetamidocephalosporanic acid as starting material and the appropriate mercaptopyrazines for the nucleophilic displacement of the acetoxy grouping, the following products were obtained:

(a) 7-phenylacetamido-3-pyrazinylthiomethyl-3-cephem-4-carboxylic acid (356/308), 68% yield, m.p. 208° C.

IR (KBr): 1775, 1710, 1660 cm$^{-1}$. NMR methylester (CDCl$_3$/DMSO-d$_6$: 5/1): 3.51δ (s, C(2)H$_2$), 3.60δ (s, C$_6$H$_5$—CH$_2$—), 3.86δ (s, COOCH$_3$), 4.28δ (dd, CH$_2$—S), 4.73δ (d, C(6)H), 5.71δ (d, C(7)H), 7.25δ (s, C$_6$H$_5$), 8.0–8.6δ (m, pyrazine protons).

(b) 7-phenylacetamido-3-(6-chlorpyrazin-2-ylthiomethyl)-3-cephem-4-carboxylic acid (356/310) 58% yield, m.p. 210° C. (ethylacetate) IR (KBr): 1775, 1710, 1665 cm$^{-1}$. NMR methylester (CDCl$_3$): 3.43δ (s, C(2)H$_2$), 3.83δ (s, COOCH$_3$ and C$_6$H$_5$—CH$_2$—), 4.23δ (dd, CH$_2$—S), 4.88δ (d, C(6)H), 5.73δ (dd, C(7)H), 7.23δ (s, C$_6$H$_5$), 8.15 and 8.24δ (two s, pyrazine protons).

(c) 7-phenylacetamido-3-(pyrazin-2-ylthiomethyl-4-oxide)-3-cephem-4-carboxylic acid (356/307) 52% yield, m.p. 215° C. IR (KRb): 1770, 1715, 1665, 1260 cm$^{-1}$. NMR methylester (CDCl$_3$/DMSO-d$_6$ 1/1): 3.44δ (s, C(2)H$_2$), 3.73δ. (s, COOCH$_3$), 3.83δ (s, C$_6$H$_5$—CH$_2$), 4.51δ (dd, CH$_2$—S), 4.91δ. (d, C(6)H), 5.88δ (dd, C(7)H), 7.16δ (s, C$_6$H$_5$), 7.8–8.3δ. (m, pyrazine protons).

EXAMPLE 3

Starting from 7-phenoxyacetamidocephalosporanic acid and the appropriate mercaptopyrazines, and by using the procedure described in the Example 1, the following products were obtained:

(a) 7-phenoxyacetamido-3-pyrazinylthiomethyl-3-cephem-4-carboxylic acid (52% yield), m.p. 190° C. IR (KRb): 1785, 1710, 1675 cm$^{-1}$.

(b) 7-phenoxyacetamido-3-(6-carboxamidopyrazin-2-ylthiomethyl)-3-cephem-4-carboxylic acid (60% yield), m.p. 140° C. IR (KBr): 1780, 1710-1650 (acid and amides) cm$^{-1}$.

(c) 7-phenoxyacetamido-3-(pyrazin-2-ylthiomethyl-4-oxide)-3-cephem-4-carboxylic acid (49% yield), m.p. 132° C.

EXAMPLE 4

Operating as described in Example 1, and using 7-(2-thienyl)-acetamido-cephalosporanic acid as starting material for the nucleophilic replacement of the acetoxy group with a suitable mercaptopyrazine, the following compounds were prepared:

(a) 7-(2-thienyl)-acetamido-3-pyrazinylthiomethyl-3-cephem-4-carboxylic acid (356/314), 78% yield, m.p. 204° (aqueous methanol). Analysis calculated for C$_{18}$H$_{16}$N$_4$O$_4$S$_3$: C 48.19, H 3.59, S 21.44. Found: C 48.38, H 3.65, S 21.06. IR (KBr): 1770, 1705, 1655 cm$^{-1}$. NMR methylester (CDCl$_3$): 3.57δ (dd, C(2)H$_2$), 3.73δ

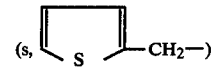
(s, $\underset{S}{\square}$—CH$_2$—)

3.82δ (s, COOCH$_3$), 4.27δ (dd, CH$_2$—S), 4.97δ (d, C(6)H), 5.26δ (dd, C(7)H), 6.8–7.0 and 7.1–7.3δ (m, thiophene protons), 8.0–8.4δ (m, pyrazine protons).

(b) 7-(2-thienyl)-acetamido-3-(6-carboxamidopyrazin-2-ylthiomethyl)-3-cephem-4-carboxylic acid (356/313) 76% yield, m.p. 150° C. (methylene chloride-methanol): Analysis calculated for C$_{19}$H$_{17}$N$_5$O$_5$S$_3$: C 46.42, H 3.48, S 19.56. Found: C 45.89, H 3.75, S 19.46. IR (KBr): 1770, 1705, 1695, 1655 cm$^{-1}$.

(c) 7-(2-thienyl)-acetamido-3-(3-methoxy-pyrazin-2-ylthiomethyl)-3-cephem-4-carboxylic acid (356/317) 69% yield, m.p. 205° C. (ethanol). Analysis calculated for C$_{19}$H$_{18}$N$_4$O$_5$S$_3$: C 47.70, H 3.79, N 11.71. Found: C 47.28, H 3.91, N 11.10. IR (KBr): 1770, 1715, 1660 cm$^{-1}$. NMR methylester (CDCl$_3$): 3.50δ (dd, C(2)H$_2$), 3.80δ

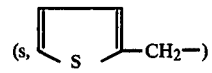
(s, $\underset{S}{\square}$—CH$_2$—)

3.87δ and 3.97δ (two s, COOCH$_3$ and OCH$_3$), 4.73δ (dd, CH$_2$—S), 4.85δ (d, C(6)H), 5.73δ (dd, C(7)H), 6.8–7.3δ (m, thiophene protons), 7.6–7.9δ (two s, pyrazine protons).

EXAMPLE 5

7-pyrazinylthioacetamidocephalosporanic acid (367/312)

To a solution of 7 g of sodium-7-chloroacetamidocephalosporanate in 20 ml of water, a solution of 2.7 g of 2-mercaptopyrazine in aqueous sodium bicarbonate was added at 0.5° C. by adjusting the pH to 7 with saturated sodium bicarbonate. After stirring for 3 hours at room temperature, the cooled solution was acidified to pH 2 and the resulting precipitate (8.3 g) was filtered and crystallized from ethanol to give 7.8 g (74% yield) of 7-pyrazinylthio amidocephalosporanic acid, m.p. 145° C.

IR (KBr): 1780, 1740, 1715, 1670, 1650 cm$^{-1}$. NMR methylester (CDCl$_3$): 2.10δ (s, CH$_3$—CO—), 3.34δ (dd, C(2)H$_2$), 3.78δ (s, COOCH$_3$ and —S—CH$_2$—CO—), 4.80δ (d, C(6)H), 4.89δ (dd, CH$_2$—OCOC(H$_3$), 5.80δ (dd, C(7)H), 8.1–8.6δ (m, pyrazine protons).

The same product was also obtained starting from both 7-bromoacetamidocephalosporanic acid and 7-iodoacetamidocephalosporanic acid.

EXAMPLE 6

By using 7-pyrazinylthioacetamidocephalosporanic acid and the appropriate mercaptopyrazines, the following products were prepared by following the procedure described above in Example 1:

(a) 7-pyrazinylthioacetamido-3-pyrazinylthiomethyl-3-cephem-4-carboxylic acid (65% yield), m.p. 175° C.

(b) 7-pyrazinylthioacetamido-3-(6-chloropyrazin-2-ylthiomethyl)-3-cephem-4-carboxylic acid (356/315), 72% yield, m.p. 165° (aqueous acetone). IR (KBr): 1810, 1715, 1690 cm$^{-1}$. NMR methylester (CDCl$_3$-DMSO-d$_6$: 1/1): 3.59$\delta$ (dd, C(2)H$_2$), 3.84$\delta$. (s, COOCH$_3$), 3.93$\delta$ (s, S—CH$_2$—CO), 4.27$\delta$ (dd, CH$_2$—S), 4.99$\delta$. (d, C(6)H), 5.68$\delta$ (dd, C(7)H), 8.1–8.5$\delta$ (m, 5 pyrazine protons).

(c) 7-pyrazinylthioacetamido-3-(pyrazin-2-ylthiomethyl-4-oxide)-3-cephem-4-carboxylic acid (356/316) 70% yield, m.p. 175° C. Analysis calculated for C$_{18}$H$_{16}$N$_6$O$_5$S$_3$: C 43.89, H 3.27, S 19.52. Found: C 43.89, H 3.73, S 18.3. IR (KBr): 1775, 1705, 1670-1660 (amides), 1265 cm$^{-1}$.

EXAMPLE 7

7-amino-3-pyrazinylthiomethyl-3-cephem-4-carboxylic acid

To a suspension of 8.16 g of 7-aminocephalosporanic acid and 4.03 g of 2-mercaptopyrazine in a 120 ml mixture of water-acetone (2:1), 5.54 g of sodium bicarbonate was added and the resultant solution was heated to 65°-70° C. for 2 hours.

The pH was maintained between 7–7.5 by occasional additions of NaHCO$_3$ or HCl. The solvent was removed in vacuo and the solution was acidified to pH 3.5 with 4 N HCl under cooling. The resulting precipitate was collected by filtration and washed, several times, with methanol. The crude material 5.6 g was suspended in water, dissolved in 6 N HCl and decolorized with charcoal, under cooling.

After filtering, the acidic solution was cooled and adjusted to pH 3.5 with 5 N NaOH. The precipitate was filtered, washed several times with water and acetone.

The product (3.35 g) was used without further purification.

IR (KBr): 1800 ($\beta$ lactam C=O), 1540 (carboxylate C=O) cm$^{-1}$ NMR (D$_2$O+DCl): 3.82$\delta$ (dd, C(2)H$_2$), 4.53$\delta$ (dd, CH$_2$—S), 8.4–9.1$\delta$ (m, pyrazine protons).

EXAMPLE 8

7-[1-(1H)-tetrazolylacetamido]-3-pyrazinylthiomethyl-3-cephem-4-carboxylic acid (356/318)

To a solution of 0.65 g of 1-(1H)-tetrazolylacetic acid and 0.7 ml of triethylamine in 25 ml of anhydrous acetone, 0.6 ml of pivaloylchloride in acetone was added at 0° C.; the reaction mixture was stirred for 30 minutes.

After filtering off triethylamine hydrochloride, the filtrate was added dropwise to a solution of 1.08 g of 7-amino-3-pyrazinylthiomethyl-3-cephem-4-carboxylic acid and 0.37 ml of triethylamine in 35 ml of a mixture of water-acetone (2:1) at 5° C., during a period of 30 minutes. The reaction mixture was stirred for 1 hour at the same temperature and for 2 additional hours at room temperature. The solvent was removed under reduced pressure and the aqueous solution was acidified to pH 1.5 with 5% HCl and extracted with ethyl acetate. The organic layer (dried) was evaporated in vacuo and the residue was washed with ethyl ether and crystallized from aqueous acetone to give 7-[1-(1H)-tetrazolylacetamido]-3-pyrazinylthiomethyl-3-cephem-4-carboxylic acid (0.9 g, 69% yield) as pale white crystals, m.p. 200° C.

Analysis calculated for C$_{15}$H$_{14}$N$_8$O$_4$S$_2$: C 41.47, H 3.28, N 25.79. Found: C 41.16, H 3.48, N 24.50. NMR methylester (CDCl$_3$/DMSO-d$_6$: 1/1): 3.57$\delta$ (dd, C(3)H$_2$), 3.84$\delta$ (s, COOCH$_3$), 4.30$\delta$ (dd, CH$_2$—S), 4.97$\delta$ (d, C(6)H), 5.28$\delta$ (s, N—CH$_2$CO), 5.66$\delta$ (dd, C(7)H), 8.05–8.60$\delta$ (m, pyrazine protons), 9.03$\delta$ (s, tetrazole protons). IR (KBr): 1770, 1705, 1680 cm$^{-1}$.

EXAMPLE 9

7-(2-Thienyl)-acetamido-3-(6-methoxypyrazin-2-ylthiomethyl)-3-cephem-4-carboxylic acid (356/321)

Operating as described in the previous example, the title compound was obtained. m.p. 195° C. Yield 81–83%

Analysis calculated for C$_{19}$H$_{18}$N$_4$O$_5$S$_3$: C 47.70, H 3.79, H 11.70. Found: C 47.79, H 3.95, H 11.50.

IR (KBr): 1775 cm$^{-1}$ $\gamma$ C=O $\beta$-lactam. 1710 cm$^{-1}$ $\gamma$ C=O acid. 1660 cm$^{-1}$ $\gamma$ C=O amide. NMR (DMSO-d$_6$) (for sodium salt): 3.39$\delta$ (dd, C(2)H$_2$), 3.75$\delta$ (s, CH$_2$—CO), 3.93$\delta$. (s, CH$_3$O), 4.40$\delta$ (broad s, CH$_2$S), 4.95$\delta$ (d, C(6)H), 5.46$\delta$ (dd, C(7)H), 6.90$\delta$ (m, 2 thiophene protons), 7.26$\delta$ (m, 1 thiophene proton), 7.90 and 8.10$\delta$ (two s, 2 pyrazine protons) and 8.97$\delta$ (d, CONH).

EXAMPLE 10

7-(2-Thienyl)-acetamido-3-(3-amino-6-methoxypyrazin-2-ylthiomethyl)-3-cephem-4-carboxylic acid Operating as described in the previous example, the title compound was obtained. M.P. 190°.

IR (KBr): 1765 cm$^{-1}$ $\gamma$ C=O $\beta$-lactam. 1665 cm$^{-1}$ $\gamma$ C=O acid. 1605 cm$^{-1}$ $\gamma$ C=O acid salt.

NMR (DMSO-d$_6$) (for sodium salt): 3.36$\delta$ (dd, C(2)H$_2$), 3.75$\delta$ (broad s, CH$_2$CO and OCH$_3$) 4.33$\delta$ (broad, CH$_2$S) 4.93$\delta$ (d, C(6)H), 5.50$\delta$ (m, C(7)H), 6.85$\delta$ (m, 2 thiophene protons); 7.30$\delta$ (m, 1 thiophene proton and 1 pyrazine proton) and 8.97$\delta$ (d, CONH).

What is claimed is:

1. A 7-acylamino-3-(substituted-pyrazinylthiomethyl)-3-cephem-4-carboxylic acid having the formula:

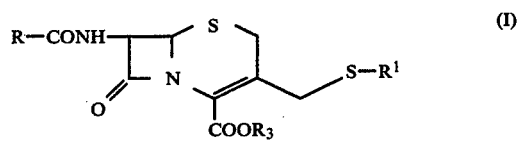

wherein R is an alkyl having from 1 to 5 carbon atoms or

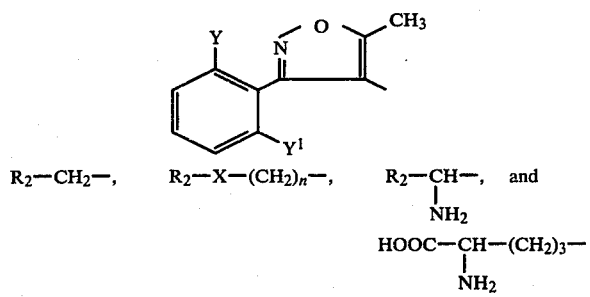

wherein
Y=Y$^1$=H $Y = Y^1 = Cl$
$Y = Cl, Y^1 = F$
$Y = H, Y^1 = Cl$, and in which n is an integer from 1 to 4, X is O or S, and R₂ is thienyl, phenyl, 1,4-cyclohexadienyl, phenoxy, pyrazinyl and substituted phenyl, thienyl, pyrazinyl and phenoxy, the substituted being selected from the group consisting of hydroxy, chlorine, bromine and alkyl and alkoxy having from 1 to 4 carbon atoms;

R₃ is alkali metal such as sodium or potassium, hydrogen, alkyl having from 1 to 4 carbon atoms, benzyl, trichloroethyl, methoxybenzyl, benzhydryl, pivaloyloxymethyl, and an alkaline earth metal;

and R¹ is a pyrazinyl of the formula:

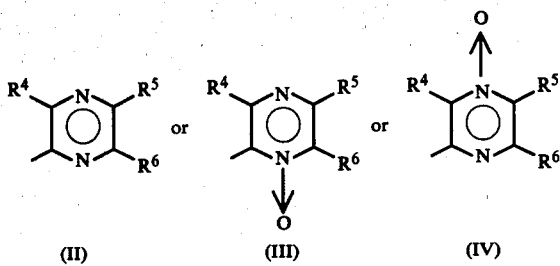

(II)        (III)        (IV)

in which R⁴, R⁵, R⁶ are equal or different and are selected from the group consisting of F, Cl, Br, hydrogen, alkyl, phenyl, cyano, thiocyano, carboxyl, carboxyalkyl, carboxamido, thiocarboxamido, hydroxy, alkoxy, thiol, alkylthio, amino, alkylamino and phenylamino, the alkyls having from 1 to 4 carbon atoms, and wherein not more than two of R⁴, R⁵ and R⁶ are hydrogen.

2. A compound as defined in claim 1, which is 7-phenylacetamido-3-(6-carboxamidopyrazin-2-ylthiomethyl)-3-cephem-4-carboxylic acid.

3. A compound as defined in claim 1, which is 7-phenylacetamido-3-(6-chloropyrazin-2-ylthiomethyl)-3-cephem-4-carboxylic acid.

4. A compound as defined in claim 1, which is 7-phenylacetamido-3-(pyrazin-2-ylthiomethyl-4-oxide)-3-cephem-4-carboxylic acid.

5. A compound as defined in claim 1, which is 7-phenoxyacetamido-3-(6-carboxamidopyrazin-2-ylthiomethyl)-3-cephem-4-carboxylic acid.

6. A compound as defined in claim 1, which is 7-phenoxyacetamido-3-(pyrazin-2-ylthiomethyl-4-oxide)-3-cephem-4-carboxylic acid.

7. A compound as defined in claim 1, which is 7-(2-thienyl)-acetamido-3-(6-carboxamidopyrazin-2-ylthiomethyl)-3-cephem-4-carboxylic acid.

8. A compound as defined in claim 1, which is 7-(2-thienyl)-acetamido-3-(3-methoxypyrazin-2-ylthiomethyl)-3-cephem-4-carboxylic acid.

9. A compound as defined in claim 1, which is 7-(pyrazinylthioacetamido-cephalosporanic acid.

10. A compound as defined in claim 1, which is 7-pyrazinylthioacetamido-3-(6-chloropyrazin-2-ylthiomethyl)-3-cephem-4-carboxylic acid.

11. A compound as defined in claim 1, which is 7-pyrazinylthioacetamido-3-(pyrazin-2-ylthiomethyl-4-oxide)-3-cephem-4-carboxylic acid.

12. A compound as defined in claim 1, which is 7-(2-thienyl)-acetamido-3-(6-methoxypyrazin-2-ylthiomethyl)-3-cephem-4-carboxylic acid.

13. A compound as defined in claim 1, which is 7-(2-thienyl)-acetamido-3-(3-amino-6-methoxypyrazin-2-ylthiomethyl)-3-cephem-4-carboxylic acid.

14. Acylamidomethyl esters, acyloxymethyl esters, 5-oxo-tetrahydro-2-furyl esters and phthalidyl esters of the acids of the formula (I) as defined in claim 1.

* * * * *

UNITED STATES PATENT AND TRADEMARK OFFICE
CERTIFICATE OF CORRECTION

PATENT NO. : 4,148,996
DATED : April 10, 1979
INVENTOR(S) : Giorgio PALAMIDESSI et al It is certified that error appears in the above-identified patent and that said Letters Patent are hereby corrected as shown below:

Column 1, lines 29 to 33 should read as follows:

-- $R_2-CH_2-$, $R_2-X-(CH_2)_n$, $R_2-\underset{NH_2}{CH}-$ and $HOOC-\underset{NH_2}{CH}-(CH_2)_3-$ --;

Column 5, line 28, "displacment" should read --displacement--;

Column 6, line 49, "(367" should read --(356--;

Column 8, line 20, "H 11.50" should read --N 11.50--.

Signed and Sealed this

Twenty-fifth Day of March 1980

[SEAL]

Attest:

SIDNEY A. DIAMOND

Attesting Officer

Commissioner of Patents and Trademarks